United States Patent
Hakamata et al.

(10) Patent No.: US 7,037,259 B2
(45) Date of Patent: May 2, 2006

(54) LIGHT SOURCE DEVICE AND IMAGE CAPTURING DEVICE

(75) Inventors: Kazuo Hakamata, Kaisei-machi (JP); Masahiro Toida, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 25 days.

(21) Appl. No.: 10/189,001

(22) Filed: Jul. 5, 2002

(65) Prior Publication Data

US 2003/0007087 A1    Jan. 9, 2003

(30) Foreign Application Priority Data

Jul. 6, 2001    (JP)    ............... 2001-206406

(51) Int. Cl.
*A61B 1/07*    (2006.01)
*F21V 8/00*    (2006.01)

(52) U.S. Cl. ............. 600/178; 362/553; 362/555; 362/582; 600/181

(58) Field of Classification Search .......... 600/178, 600/180, 181; 385/141–145; 252/301.17; 362/582, 553, 555, 583

See application file for complete search history.

(56) References Cited

U.S. PATENT DOCUMENTS

| | | | | |
|---|---|---|---|---|
| 4,812,013 | A * | 3/1989 | Aurouet et al. ............... 385/12 |
| H1364 | H * | 10/1994 | Toeppen ......................... 372/6 |
| 5,579,429 | A * | 11/1996 | Naum ........................... 385/143 |
| 6,139,174 | A * | 10/2000 | Butterworth ................ 362/555 |
| 6,217,510 | B1 * | 4/2001 | Ozawa et al. ............... 600/129 |
| 6,258,576 | B1 * | 7/2001 | Richards-Kortum et al. ......... 435/40.52 |
| 6,272,269 | B1 * | 8/2001 | Naum ........................... 385/43 |
| 6,299,338 | B1 * | 10/2001 | Levinson et al. ............. 362/559 |
| 6,363,088 | B1 * | 3/2002 | Alphonse et al. ............... 372/6 |
| 2001/0008571 | A1 * | 7/2001 | Chivers ......................... 385/75 |
| 2002/0045811 | A1 * | 4/2002 | Kittrell et al. ............... 600/407 |
| 2003/0191368 | A1 * | 10/2003 | Wang et al. ................. 600/160 |
| 2004/0076395 | A1 * | 4/2004 | Poisel et al. ................. 385/141 |
| 2004/0143157 | A1 * | 7/2004 | Doguchi et al. ............. 600/109 |

FOREIGN PATENT DOCUMENTS

EP    0982924 A2 *    7/1999

(Continued)

OTHER PUBLICATIONS http://www.sumita-opt.co.jp/LUMI1E.HTM, "New Active Fluorescent Glasses", May 7, 1997, pp. 1-4.*

(Continued)

*Primary Examiner*—John P. Leubecker
(74) *Attorney, Agent, or Firm*—Sughrue Mion, PLLC (57) ABSTRACT

A light source device for use in an image capturing device such as an endoscope capable of reducing size and cost, and preventing heat generation at an illuminated position. An illumination unit of the endoscope includes LED light sources for emitting ultraviolet light, fluorescent fibers for generating red, green and blue light respectively by irradiation of the ultraviolet light, a sampling light source, and an excitation light source. Upon capturing a normal image, the ultraviolet light is emitted sequentially from the LED light sources to cause the fluorescent fibers to generate the red, green and blue light. The light of each color is passed through a light guide and irradiated on an observation area of a living body. Thereafter, reflected images attributable to the light of each color are captured with a CCD image capturing element of a charge multiplying type, and captured images are displayed on a monitor.

16 Claims, 4 Drawing Sheets

FOREIGN PATENT DOCUMENTS

| JP | 6-51126 | * | 2/1994 |
| JP | 09073807 A | * | 3/1997 |
| JP | 2000285718 A | * | 10/2000 |

OTHER PUBLICATIONS http://www.sumita-opt.co.jp/BULKFIB.HTM, "Bulk Fiber Bundle", Mar. 2001, pp. 1-2.* http://www.sumita-opt.co.jp/en/functional/functional04.htm, "Lumilass", pp. 1-11.* http://www.photonics.com/spectra/newprods/XQ/ASP/newprodido.389/QX/read.htm, "Photonics", May 1997, 1 page.* http://www.dnlabs.com/new_page_5.htm, "Polyescent", pp. 1-3.*

* cited by examiner

LIGHT SOURCE DEVICE AND IMAGE CAPTURING DEVICE

BACKGROUND OF THE INVENTION

1. Field of the Invention

The present invention relates to a light source device using a solid-state light-emitting element such as a light-emitting diode (LED), a super luminescence diode (SLD) or a laser diode (LD), and to an image capturing device using the light source device.

2. Description of the Related Art

Conventionally, image capturing devices such as an endoscope, which uses a solid-state image capturing element such as a charge-coupled device (CCD) for converting an optical image into electrical signals, have been utilized in the medical field for capturing an optical image of an observation area. Image data outputted from the solid-state image capturing device have an advantage that a plurality of people can observe the image data simultaneously by means of displaying the data on a monitor or the like. Moreover, the image data can be subjected to a variety of image processing prior to display, whereby it is also possible to display histopathologies on the monitor, which are unrecognizable with the naked eye, thus contributing largely to developments in medical science.

In the endoscope as described above, a light source such as a xenon lamp, a halogen lamp or metal halides (hereinafter collectively referred to as the xenon lamp, etc.) is used to illuminate the observation area. It is possible to irradiate sufficient illumination light onto the observation area by use of the above-mentioned light source.

However, since the above-mentioned light source device including the xenon lamp, etc. is large and expensive, the image capturing device itself becomes large and expensive. Moreover, the illumination light emitted from the above-described light source device contains long-wavelength components such as infrared light. Accordingly, a large amount of heat is generated in a position where the illumination light is irradiated. For this reason, in the endoscope provided with the solid-state image capturing element being disposed at an inserting portion to be inserted into a living body, there is also a problem that dark noise is generated due to the heat and the noise is included in output data, whereby an S/N ratio of an obtained image is deteriorated.

SUMMARY OF THE INVENTION

The present invention has been made in consideration of the foregoing problems. It is an object of the present invention to provide a small, inexpensive and less heat-generating light source device and an image capturing device using the light source device.

The light source device according to the present invention includes at least one light-emitting source including a solid-state light-emitting element for emitting excitation light, and at least one fluorescent fiber for generating illumination light in a given wavelength range owing to irradiation of the excitation light emitted from the solid-state light-emitting element and for emitting the illumination light from one end thereof.

To be more precise, a light-emitting diode (LED), a laser diode (LD) and a super luminescence diode (SLD) can be used as the "solid-state light-emitting element".

Although it is possible to use only one solid-state light-emitting element for the "light-emitting source", it is also possible to use a light-emitting element array in which a plurality of solid-state light-emitting elements are arranged in a line or in an array so as to gain more luminous energy.

As for the "fluorescent fiber", it is possible to use fluorescent glass, which emits light in wavelength ranges corresponding to respective colors of R, G and B owing to irradiation of excitation light in an ultraviolet wavelength range from 200 to 400 nm, for example (such as "Lumillas" made by Sumita Optical Glass, Inc.).

In the light source device according to the present invention, it is preferable to form the solid-state light-emitting element with either the SLD or the LD and to connect the other end of the fluorescent fiber to an emitting end face of the SLD or the LD.

Moreover, in the light source device according to the present invention, it is preferable that the light source device includes three types of the fluorescent fibers for emitting the illumination light in the wavelength ranges corresponding to the respective colors of R, G and B owing to irradiation of the excitation light, and includes three light-emitting sources for irradiating the excitation light onto the respective fluorescent fibers.

In addition, in the light source device according to the present invention, it is preferable that the fluorescent fibers are single fibers.

Moreover, in this case, it is preferable that a core diameter of each single fiber is within 400 μm.

An image capturing device according to the present invention includes the light source device according to the present invention for irradiating the illumination light onto the observation area, and a solid-state image capturing means of a charge multiplying type for capturing an optical image based on reflected light emitted from the observation area owing to irradiation of the illumination light and thereby obtaining output data.

In the image capturing device according to the present invention, it is preferable that part or all of the light source device and the solid-state image capturing means constitute a mode of an endoscope to be inserted into a living body.

A solid-state image capturing element of a charge multiplying type multiplies captured signal electrical charges in accordance with a multiplication factor based on a multiplication factor control signal, as disclosed in Japanese Unexamined Patent Publication No. 7(1995)-176721, for example. It is possible to enhance and to control the image capturing sensitivity of an image capturing device by means of loading this solid-state image capturing element on a variety of image capturing devices such as an endoscope. In other words, if luminous energy is inadequate for image capturing by use of a conventional image capturing element, it is possible to display a visible image by capturing an image using this solid-state image capturing device. In addition, it is also possible to control the image capturing sensitivity appropriately according to an image capturing condition. Such a solid-state image capturing element of a charge multiplying type provided with charge multiplying means is referred to as a charge multiplying detector CCD (CMD-CCD). The CMD-CCD is designed to cause collisions between conductive electrons and atoms in an intense electric field area, whereby signal electrical charges are multiplied by a charge multiplying effect generated in accordance with such ionization and to enhance the image capturing sensitivity of the image capturing element accordingly.

In the solid-state image capturing element of the charge multiplying type, the charge multiplying means multiplies the signal electrical charges in advance of an electrical charge detection circuit provided for converting the signal electrical charges sequentially into signal voltages being retrieved as output signals. Accordingly, the charge multiplying means does not multiply read-out noises which are generated in the electrical charge detection circuit. Therefore, the read-out noises do not change if the signal electrical charges are multiplied. Hence, it is possible to enhance an S/N ratio of the output signal.

In this way, by use of the solid-state image capturing element of the charge multiplying type, the S/N ratio of the output signal can be enhanced. Moreover, the multiplication factor of the signal electrical charges is variable with the multiplication factor control signal. Accordingly, the image capturing sensitivity is controllable in the image capturing device loading the solid-state image capturing element of the charge multiplying type.

Note that an endoscope using the above-described solid-state image capturing element of the charge multiplying type is disclosed in Japanese Unexamined Patent Publication No. 2001-29313.

According to the light source device of the present invention, the excitation light emitted from at least one light-emitting source made of a solid-state light-emitting element is irradiated onto the fluorescent fiber, whereby illumination light in the given wavelength range is emitted from one end of the fluorescent fiber. In this way, since the light source device according to the present invention applies the light-emitting source made of the solid-state light-emitting element, it is possible to downsize the light source device as compared to the above-mentioned light source device using the xenon lamp, etc. Moreover, the solid-state light-emitting element is considerably less expensive than the xenon lamp, etc. Accordingly, it is possible to reduce the cost of the light source device as compared to the light source device using the xenon lamp, etc. even if a plurality of solid-state light-emitting elements is arrayed.

In addition, a material not generating light in a long-wavelength range, such as infrared light, may be used as the fluorescent fiber, whereby it is possible to prevent heat generation in positions of irradiation of the illumination light emitted from the light source device of the present invention. Therefore, when the light source device according to the present invention is applied to an image capturing device using the solid-state image capturing element, it is possible to prevent generation of dark noise attributable to the heat in the irradiated positions. As a result, an image with a fine S/N ratio can be obtained.

Moreover, since an emitting portion of the SLD and the LD has a small diameter, the excitation light can be made incident on the fluorescent fiber efficiently by connecting the other end of the fluorescent fiber directly to the emitting end face. As a result, it is possible to magnify the luminous energy of the illumination light.

Furthermore, a set of fluorescent fibers are prepared for emitting the illumination light in the wavelength ranges corresponding to the respective colors of R, G and B and the excitation light is irradiated onto the respective fluorescent fibers from three light-emitting sources, whereby white illumination light can be obtained.

Here, upon connecting the fluorescent fiber to the emitting end face of the SLD or the LD, incident efficiency is deteriorated by cladding portions between cores of strands if the fluorescent fiber is a bundled fiber. Therefore, such cladding portions are eliminated by use of a single fiber as the fluorescent fiber, whereby incident efficiency of the excitation light can be enhanced and the luminous energy of the illumination light can be thereby magnified.

When the single fiber is used, the fiber tends to crack easily if a core diameter thereof is relatively large. Therefore, by setting the core diameter thereof within 400 μm, it is possible to prevent the single fiber from cracking easily.

Moreover, when the light source device of the present invention is applied to the image capturing device, the luminous energy of the illumination light irradiated onto the observation area is smaller than the case of using the light source device of the xenon lamp, etc. Accordingly, there is a risk that an S/N ratio of an obtained image is deteriorated. Therefore, a solid-state image capturing element of a charge-multiplying type is used as the solid-state image capturing element for capturing the optical image of the observation area. In this way, if the luminous energy of the illumination light is weak, it is possible to enhance the image capturing sensitivity by multiplying the signal electrical charges obtained by image capturing. Accordingly, it is possible to enhance the S/N ratio of the obtained image when the light source device of the present invention is used.

In the meantime, if the illumination light emitted from the fluorescent fiber is introduced into a living body by use of the single fiber, it is possible to reduce a diameter of an inserting portion to be inserted into the living body.

DESCRIPTION OF THE PREFERRED EMBODIMENTS

Figure 1:
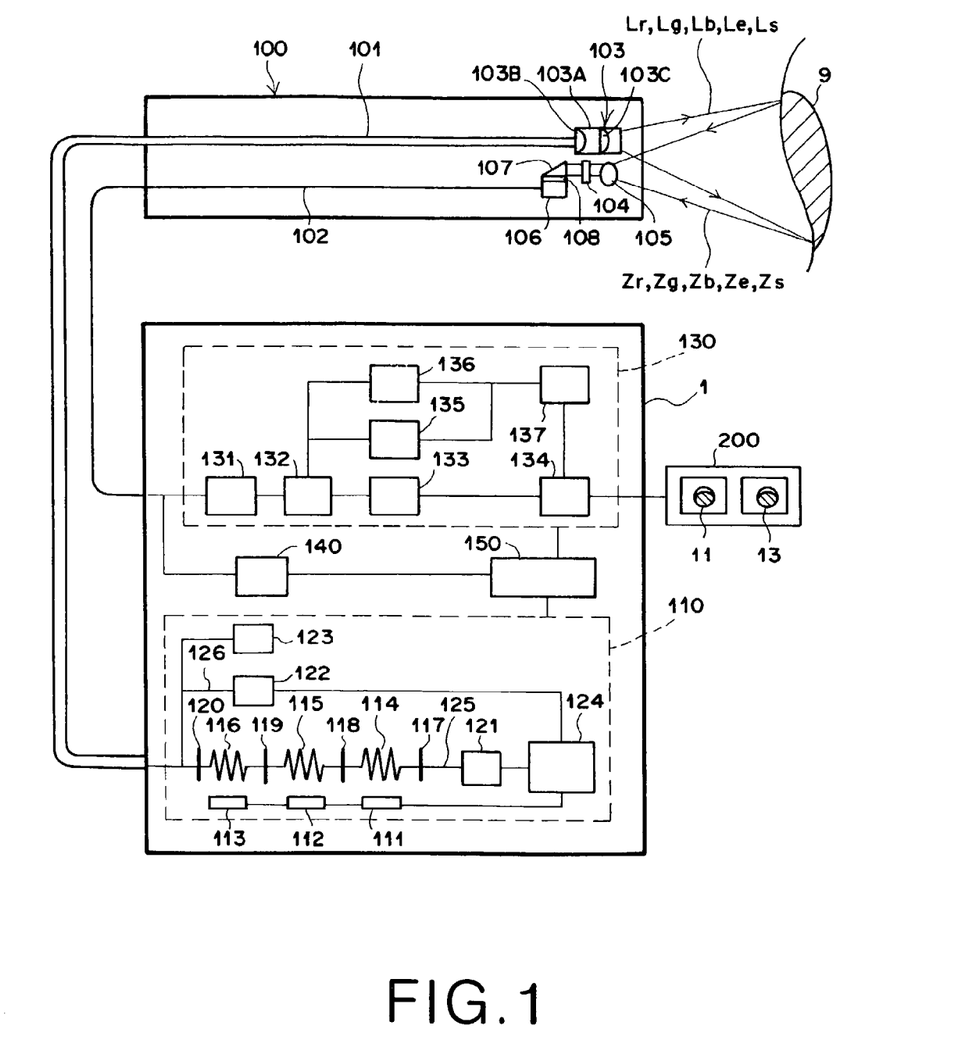
FIG. 1 is a schematic constitutional view showing a constitution of an endoscope using a light source device according to a first embodiment of the present invention.

Now, embodiments of the present invention will be described with reference to the accompanying drawings. FIG. 1 is a schematic constitutional view showing a constitution of an endoscope using a light source device according to a first embodiment of the present invention. As shown in FIG. 1, the endoscope adopts a frame sequential method, in which R light (red light) Lr, G light (green light) Lg and B light (blue light) Lb collectively being illumination light, sampling light (near infrared light) Ls and excitation light Le are sequentially irradiated on an observation area of a living body 9 and a reflected image being reflected by the observation area of the living body 9 and a fluorescent image generated at the observation area of the living body 9 are captured with a CCD image capturing element of a charge multiplying type, whereby an image of the observation area is displayed on a monitor as a color image. The endoscope includes an endoscope inserting portion 100 having the CCD image capturing element on a tip thereof, the endoscope inserting portion 100 being inserted into a region of a patient's body suspected to be a nidus of disease, an image data processor unit 1 for processing image data representing information obtained from the observation area of the living body 9, and a monitor 200 for displaying the image data processed by the image data processor unit 1 as a visible image.

The endoscope inserting portion 100 includes a light guide extending inside toward a tip thereof, and a CCD cable 102. On tips of the light guide 101 and the CCD cable 102, i.e. on a tip of the endoscope inserting portion 100, provided are an illumination optical system 103, an excitation light cutoff filter 104 and a condenser lens 105.

The illumination optical system 103 includes a mirror tube 103A with a mirror inner surface, and two illumination lenses 103B and 103C.

On the tip of the CCD cable 102, connected is the CCD image capturing element 106 of a charge multiplying type provided with a mosaic filter 108 on a tip thereof, which is formed by mosaic combination of minute bandwidth filter elements. Moreover, a prism 107 is fitted to the CCD image capturing element 106. The excitation light cutoff filter 104 is a long pass filter which transmits all kinds of fluorescent light having a wavelength at 420 nm and above. Another end of the light guide 101 opposite to the above-mentioned tip is connected to an illumination unit 110 to be described later. Note that the CCD image capturing element 106 is designed to capture reflected images Zr, Zg and Zb obtained by irradiating the R light Lr, the G light Lg and the B light Lb onto the observation area of the living body 9, a fluorescent image Ze generated from the observation area of the living body 9 owing to irradiation of the excitation light Le, and a reflected image Zs obtained by irradiating the sampling light Ls onto the observation area of the living body 9 (the images Zr, Zg, Zb, Ze and Zs will be hereinafter collectively referred to as optical images). The CCD image capturing element 106 further converts the optical images into digital values and outputs the digital values as image data.

Figure 2:
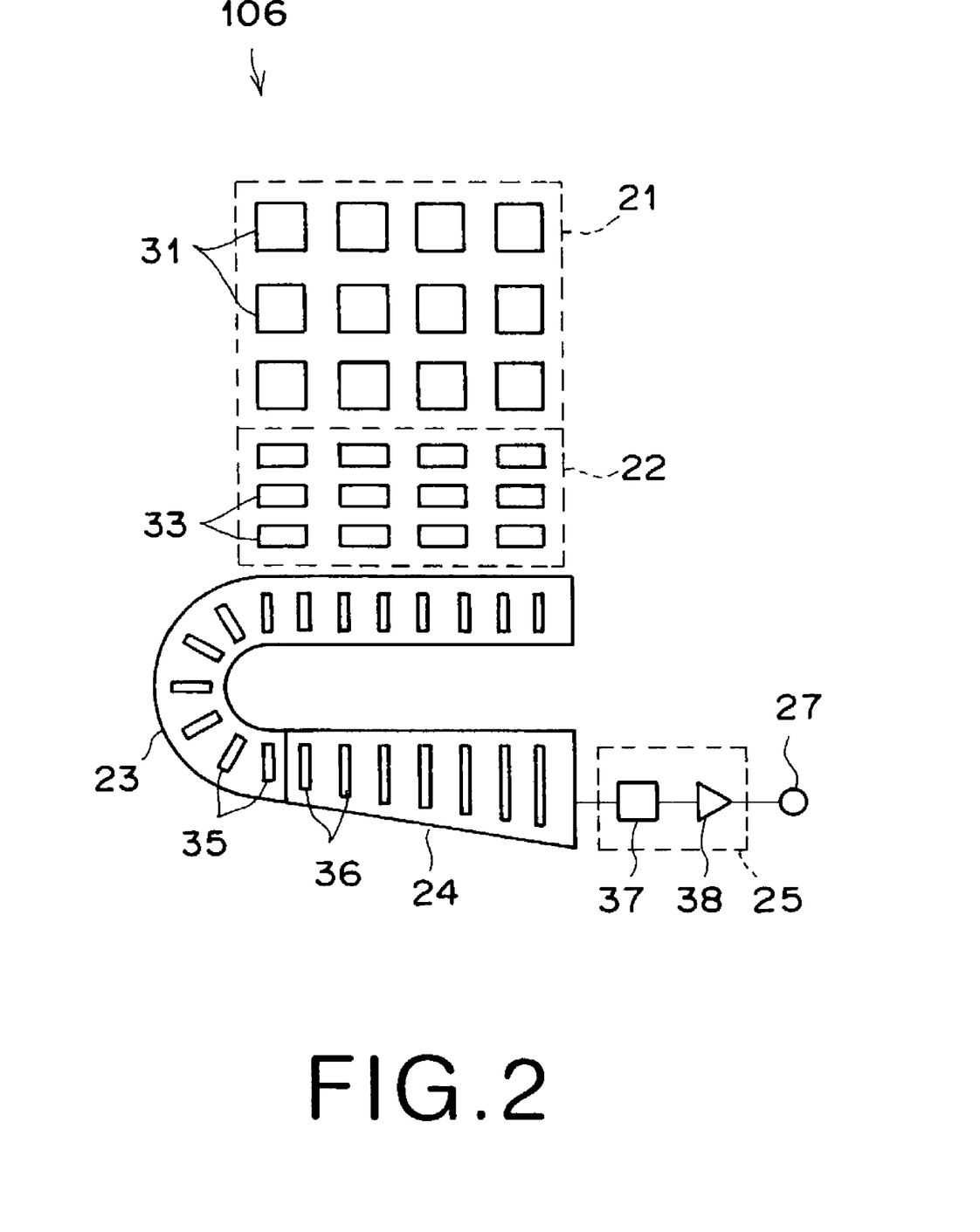
FIG. 2 is a view showing a constitution of a CCD image capturing element.

FIG. 2 is a view showing a constitution of the CCD image capturing element 106. As shown in FIG. 2, the CCD image capturing element 106 is a CMD-CCD image capturing element of a frame transfer type, which includes a light receiving unit 21 for converting the captured optical images into signal electrical charges, an accumulator unit 22 for temporarily accumulating and transferring the signal electrical charges, a horizontal transfer unit 23 for performing horizontal transfer of the signal electrical charges, a charge multiplying unit 24 for multiplying the signal electrical charges in accordance with a multiplication factor control signal inputted, and an output unit 25 for converting the signal electrical charges into signal voltages, amplifying the signal voltages and outputting the signal voltages from an output terminal 27 to an image processing unit 130.

The light receiving unit 21 is composed of a matrix of vertical n pieces and horizontal n' pieces of vertical transfer CCD's 31, which perform photoelectric conversion and vertical transfer of the signal electrical charges. For the purpose of facilitating explanation, FIG. 2 illustrates the light receiving unit 21 composed of three vertical pieces and four horizontal pieces of the vertical transfer CCD's 31. However, an actual CCD image capturing element 106 includes several hundreds of the vertical transfer CCD's 31 being provided vertically and horizontally.

The accumulator unit 22 is shielded from light with a thin metallic film or the like. The accumulator unit 22 is composed of vertical transfer CCD's 33 for performing temporary accumulation and vertical transfer of the signal electrical charges. The horizontal transfer unit 23 is composed of horizontal transfer CCD's 35.

The charge multiplying unit 24 is composed of m pieces of charge multiplying cells 36. The signal electrical charges inputted to the charge multiplying unit 24 are multiplied and transferred sequentially based on the multiplication factor control signals, which are continuous pulse signals. The charge multiplying cell 36 is designed to cause collisions between conductive electrons and atoms in an intense electric field area, whereby the inputted signal electrical charges are multiplied for output by use of a charge multiplying effect generated in accordance with ionization. A multiplication factor thereof varies according to signal characteristics of the multiplication factor control signals. Note that the accumulator unit 22, the horizontal transfer unit 23 and the charge multiplying unit 24 are illustrated simply in FIG. 2 as similar to the light receiving unit 21.

The output unit 25 includes a charge detection unit 37 for converting the signal electrical charges into the signal voltages (output signals), and an output amplifier 38 for amplifying the output signals.

Figure 3:
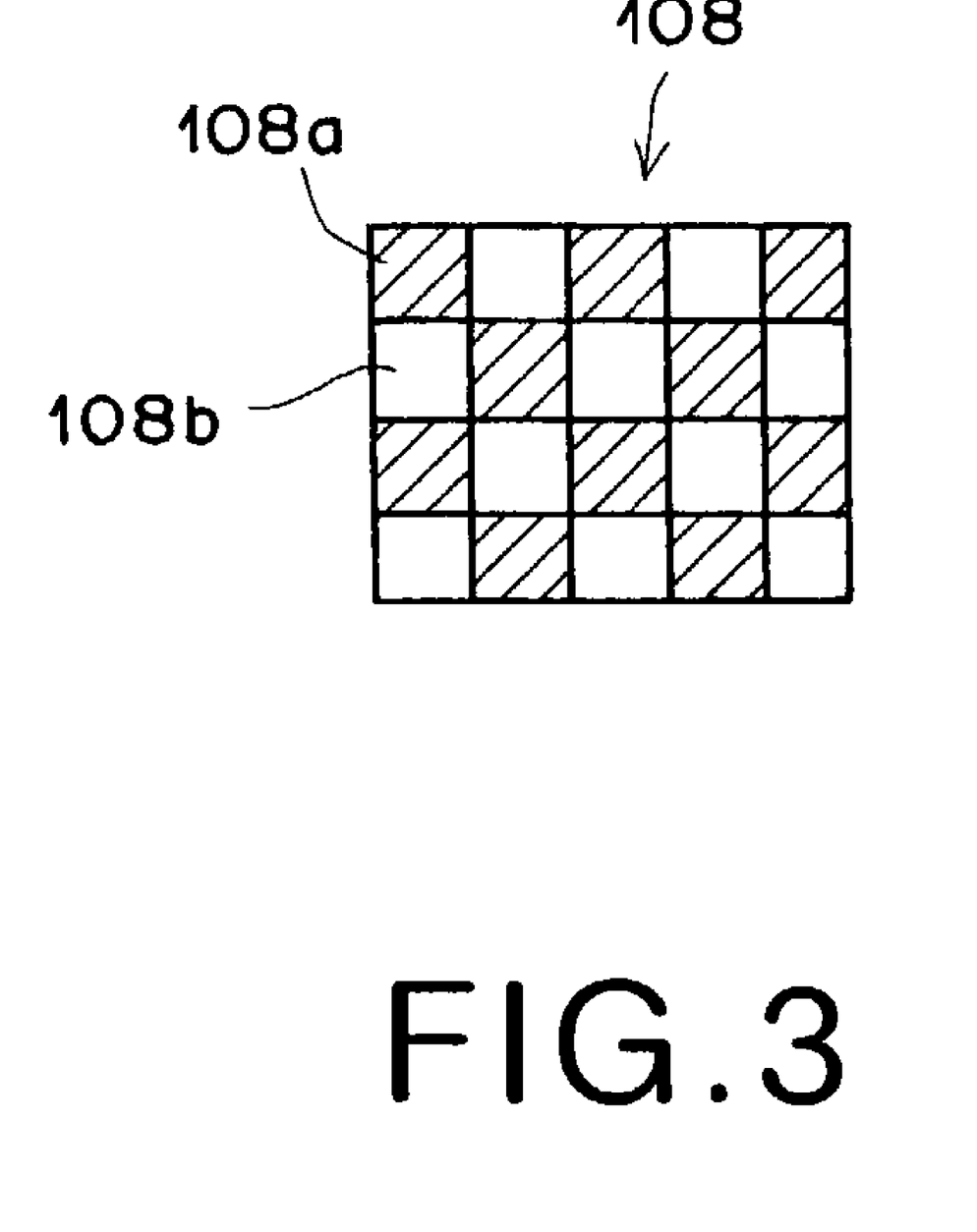
FIG. 3 is a view showing a constitution of a mosaic filter.

FIG. 3 is a view showing a constitution of the mosaic filter 108. As shown in FIG. 3, in the mosaic filter 108, broadband filter elements 108a which transmit light in a wavelength range from 400 nm to 900 nm, and narrow-band filter elements 108b which transmit light in a wavelength range from 430 nm to 530 nm are combined alternately. Each of the respective bandwidth filter elements 108a and 108b corresponds one-on-one to each pixel of the CCD image capturing element 106.

The image data processor unit 1 is composed of the illumination unit 110 for emitting the illumination light, the image processing unit 130 for performing image processing to display the image data, a CCD controller 140 for controlling operations of the CCD image capturing elements 106, and a controller 150 for controlling the respective units and the CCD controller 140.

The illumination unit 110 includes three LED light sources 111, 112 and 113 each formed in a manner that a plurality of ultraviolet-ray-emitting LED's are disposed in an array, serially-connected fluorescent fibers 114, 115 and 116 for emitting the R light Lr, the G light Lg and the blue light Lg, respectively in accordance with irradiation of the ultraviolet light emitted from the LED light sources 111, 112 and 113, dichroic mirrors 117, 118, 119 and 120 for controlling reflection and transmission of the R light Lr, the G light Lg and the blue light Lg emitted from the fluorescent fibers 114, 115 and 116, the ultraviolet light respectively emitted from the LED light sources 111, 112 and 113 and the sampling light Ls to be described later, a sampling light source 121 made of an SLD for emitting the sampling light Ls, an excitation light source 122 made of a GaN-LD for emitting the excitation light Le, a power monitor 123 for monitoring luminous energy of the light emitted from the LED light sources 111, 112 and 113, the sampling light source 121 or the excitation light source 122, and a power source 124 for light sources for supplying electricity to the LED light sources 111, 112 and 113, the sampling light source 121 and the excitation light source 122.

Note that a fiber 125 for guiding the sampling light Ls emitted from the sampling light source 121 to the fluorescent fiber 114, a fiber 126 for guiding the excitation light Le emitted from the excitation light source 122 to the light guide 101, and the fluorescent fibers 114, 115 and 116 are made of single fibers with core diameters within 400 μm. Moreover, a single fiber continuous with the fluorescent fiber 116 and a single fiber continuous with the fiber 126 with the core diameter within 400 μm are included in the light guide 101.

The fluorescent fibers 114, 115 and 116 are made of fluorescent glass which emits light in wavelength ranges corresponding to the respective R, G and B colors in accordance with irradiation of the ultraviolet light (such as "Lumillas" made by Sumita Optical Glass, Inc.), and are wound as coils so as to receive the ultraviolet light emitted from the LED light sources 111, 112 and 113 efficiently.

The dichroic mirror 117 has a characteristic to transmit only the light in the wavelength range of the sampling light Ls out of the light emitted from the sampling light source 121 and guided with the fiber 125, and a characteristic to reflect the light in the wavelength range of the R light Lr generated by the fluorescent fiber 114. The dichroic mirror 118 has a characteristic to transmit the light in the wavelength ranges of the R light Lr generated by the fluorescent fiber 114 and the sampling light Ls guided through the fluorescent fiber 114, and a characteristic to reflect the light in the wavelength range of the G light Lg generated by the fluorescent fiber 115. The dichroic mirror 119 has a characteristic to transmit the light in the wavelength ranges of the G light Lg generated by the fluorescent fiber 115, the R light Lr guided through the fluorescent fiber 115 and the sampling light Ls, and a characteristic to reflect the light in the wavelength range of the B light Lb generated by the fluorescent fiber 116. The dichroic mirror 120 has a characteristic to transmit the light in the wavelength ranges of the R light Lr, the G light Lg, the B light Lb and the sampling light Ls guided through the fluorescent fiber 116, and a characteristic to reflect the light in the wavelength range of the ultraviolet light.

The sampling light source 121 emits the light containing the sampling light in a wavelength range from 750 nm to 900 nm. Note that the sampling light source 121 is made of an SLD and an emitting end face thereof is smaller than an LED. Accordingly, the emitting end face is connected to the fiber 125 directly.

The excitation light source 122 emits the light containing the excitation light Le in a wavelength range from 400 nm to 420 nm. Note that the excitation light source 122 is made of an LD and an emitting end face thereof is smaller than an LED. Accordingly, the emitting end face is connected to the fiber 126 directly.

The power monitor 123 monitors the luminous energy of the light respectively emitted from the LED light sources 111, 112 and 113, the sampling light source 121 and the excitation light source 122. The power monitor 123 further controls the electricity to be supplied from the power source 124 for light sources to the respective light sources such that the luminous energy is set to a predetermined value.

The controller 150 controls the illumination unit 110 thus constituted to perform lighting with the respective light sources 111, 112, 113, 121 and 122 so as to repeat a cycle of lighting the respective light sources 111, 112, 113, 121 and 122 for certain time periods according to this order.

By controlling the lighting cycle for the respective light sources 111, 112, 113, 121 and 122 of the illumination unit 110 as described above, an irradiation cycle of the R light Lr, the G light Lg, the B light Lb, the sampling light Ls and the excitation light Le onto the observation area of the living body 9 is repeated. Here, during a period when the R light Lr, the G light Lg, the B light Lb and the sampling light Ls are irradiated onto the observation area of the living body 9, the CCD image capturing element 106 detects the optical images passing only through the broad-band filter elements 108a of the mosaic filter 108. Meanwhile, during a period when the excitation light Le is irradiated, the CCD image capturing element 106 detects the fluorescent images passing through the broad-band filter elements 108a and the narrow-band filter elements 108b, respectively.

The CCD controller 140 is designed to output an operation control signal for controlling operation timing of the CCD image capturing element 106 and the multiplication factor controlling signal for controlling the multiplication factor of the charge multiplying unit 24. It is possible to control the multiplication factor of the electrical charges at the charge multiplying unit 24 by outputting the multiplication factor controlling signal having a predetermined peak value set by a user.

The image processing unit 130 includes a signal processing circuit 131 for processing electric signals obtained by the CCD image capturing element 106, an A/D converter circuit 132 for digitizing image data obtained by the signal processing circuit 131, an image memory 133 for saving the image data of the respective colors obtained from the reflected images Zr, Zg and Zb, a fluorescent image memory 135 for respectively saving broad-band fluorescent image data representing a broad-band fluorescent image and narrow-band fluorescent image data representing a narrow-band fluorescent image obtained from the fluorescent image Ze as will be described later, an image memory 136 for saving sampling image data obtained from the reflected image Zs, an image generating circuit 137 for obtaining computed values by computing a ratio of respective pixel values corresponding to the broad-band fluorescent image represented by the broad-band fluorescent image data and the narrow-band fluorescent image represented by the narrow-band fluorescent image data, generating color image data representing a color image by allotting color information corresponding to the sizes of the computed values, generating luminance image data representing a luminance image by allotting luminance information corresponding to the sizes of respective pixel values of the sampling image represented by the sampling image data, and thereby generating and outputting synthesized image data representing a fluorescent diagnostic image by synthesizing the color image data and the luminance image data, and a video signal processing circuit 134 for converting the image data for three colors synchronized and outputted from the image memory 133 and the synthesized image data generated by the image generating circuit 137 into video signals to be outputted.

Note that the image processing circuit 137 may be also designed to obtain computed values by computing ratios of respective pixel values between the sampling image represented by the sampling image data stored in the image memory 136 and any one of the broad-band fluorescent image represented by the broad-band fluorescent image data and the narrow-band fluorescent image represented by the narrow-band fluorescent image data respectively stored in the fluorescent image memory 135, and to generate the color image data representing the color image by allotting color information corresponding to the sizes of the computed values.

Now, description will be made regarding an operation of the endoscope according to the first embodiment. In the endoscope according to the present embodiment, image capturing of the reflected images Zr, Zg and Zb, image capturing of the reflected image Zs and image capturing of the fluorescent image Ze are performed by time division, whereby a normal image 11 based on the reflected images Zr, Zg and Zb and a fluorescent diagnostic image 13 based on the reflected image Zs and the fluorescent image Ze are displayed on the monitor 200. In order to capture the respective optical images by time division, lighting of the LED light sources 111, 112 and 113, the sampling light source 121 and the excitation light source 122 in the illumination unit 110 is controlled by the controller 150, whereby the R light Lr, the G light Lg, the B light Lb, the sampling light Ls and the excitation light Le are irradiated sequentially onto the observation area of the living body 9.

First, an operation for displaying the normal image 11 will be described. The LED light source 111 is driven to begin with, whereby the ultraviolet light emitted from the LED light source 111 is irradiated onto the fluorescent fiber 114. In this way, the R light Lr is generated by the fluorescent fiber 114 and the R light Lr is transmitted through the dichroic mirrors 118, 119 and 120 and guided with the light guide 101. Further, the R light Lr is transmitted through the illumination optical system 103 and irradiated onto the observation area of the living body 9.

The reflected image Zr attributable to the R light Lr reflected by the observation area of the living body 9 is condensed with the condenser lens 105, transmitted through the excitation light cutoff filter 104 and reflected by the prism 107, whereby the reflected image Zr is transmitted through the broad-band filter elements 108a of the mosaic filter 108 and formed into an image on the CCD image capturing element 106.

At the CCD image capturing element 106, the reflected image Zr is received by the vertical transfer CCD's 31 of the light receiving unit 21 and subjected to photoelectric conversion, whereby the reflected image Zr is converted into electric signals corresponding to light intensity.

After passage of a given time period, the LED light source 111 is turned off and the LED light source 112 is turned on. In the event of switching the LED lighting, the signal electrical charges accumulated in the vertical transfer CCD's 31 are transferred to the vertical transfer CCD's 33 of the accumulator unit 22.

The signal electrical charges transferred to the vertical transfer CCD's 33 of the accumulator unit 22 are vertically transferred in parallel, and transmitted sequentially to the horizontal transfer CCD's 35 of the horizontal transfer unit 23.

When the signal electrical charges for one horizontal line pixels are inputted to the horizontal transfer unit 23, the signal electrical charges are transferred horizontally therein. In this way, the signal electrical charges are transferred sequentially to the charge multiplying cells 36 of the charge multiplying unit 24. In the charge multiplying cells 36, the signal electrical charges are transferred sequentially while being multiplied based on the multiplication factor control signal. The signal charges outputted from the last charge multiplying cell 36 to the output unit 25 disposed on the right end are converted into the signal voltages with the charge detection unit 37, amplified with the output amplifier 38, and then outputted from the output terminal 27 as output signals.

Thereafter, the signal electrical charges for one subsequent horizontal line are transferred from the accumulator unit 22 to the horizontal transfer unit 23. The signal electrical charges are read out sequentially from the pixel at the bottom left side of the light receiving unit 10 toward the right direction by repeating the operation as described above. When the signal electrical charges for one horizontal line are read out, then the signal electrical charges for one horizontal line immediately above are read out. Accordingly, all the signal electrical charges for forming an R image are thus read out by shifting the lines in turn.

When the above-described operation for reading out the signal electrical charges accumulated in the accumulator unit 22 is in progress, the LED light source 112 is turned on instead of the LED light source 111, whereby the ultraviolet light emitted from the LED light source 112 is irradiated onto the fluorescent fiber 115. In this way, the G light Lg is generated by the fluorescent fiber 115 and the G light Lg is transmitted through the dichroic mirrors 119 and 120 and guided with the light guide 101. Further, the G light Lg is transmitted through the illumination optical system 103 and irradiated onto the observation area of the living body 9. The reflected image Zg attributable to the G light Lg reflected by the observation area of the living body 9 is received by the CCD image capturing element 106 as similar to the case in the reflected image Zr. Moreover, an image capturing operation at the CCD image capturing element 106 is conducted based on the operation control signal inputted from the CCD controller 140.

Output data of the R image outputted from the CCD image capturing element 106 are processed by the signal processing circuit 131 of the image processing unit 130, then converted into digital signals by the A/D converter circuit 132, and stored into a storage area for the R image data in the image memory 133.

Thereafter, G image data and B image data are obtained by similar operations and are respectively stored in a storage area for the G image data and a storage area for the B image data in the image memory 133.

When the image data for three colors are stored in the image memory 133, those data are synchronized and outputted in line with display timing. The output data are then converted into video signals by the video signal processing circuit 134 and outputted to the monitor 200, whereby the video signals are displayed as the normal image 11, which is a color image.

Next, description will be made regarding an operation for displaying the fluorescent diagnostic image 13. Subsequent to turning the LED light sources 111, 112 and 113 on and off, the sampling light source 121 is turned on. The light from the sampling light source 121 is guided by the fiber 125, and the sampling light Ls in the wavelength range of near infrared light is only transmitted through the dichroic mirror 117 and guided by the light guide 101, whereby the sampling light Ls, which is the near infrared light, is irradiated onto the observation area of the living body 9.

The reflected image Zs of the sampling light Ls reflected by the observation area of the living body 9 is condensed with the condenser lens 105, transmitted through the excitation light cutoff filter 104 and reflected by the prism 107, whereby the reflected image Zs is transmitted through the broad-band filter elements 108a of the mosaic filter 108 and formed into an image on the CCD image capturing element 106.

At the CCD image capturing element 106, the reflected image Zs is received and subjected to photoelectric conversion, whereby the reflected image Zs is converted into electric signals and inputted to the image processing unit 130 as similar to the foregoing. The electric signals inputted to the image processing unit 130 are processed by the signal processing circuit 131, then converted into digital signals by the A/D converter circuit 132, and stored into the image memory 136 as the sampling image data.

Next, description will be made regarding an operation for capturing the fluorescent image Ze attributable to the excitation light Le. Subsequent to turning the sampling light source 121 on and off, the excitation light source 122 is turned on. The excitation light Le emitted from the excitation light source 122 is guided by the fiber 126 and the light guide 101, and is irradiated onto the observation area of the living body 9.

The fluorescent image Ze from the observation area of the living body 9 generated by irradiation of the excitation light Le is condensed with the condenser lens 105, transmitted through the excitation light cutoff filter 104 and reflected by the prism 107, whereby the fluorescent image Ze is transmitted through the broad-band filter elements 108a and the narrow-band filter elements 108b of the mosaic filter 108 respectively and formed into an image on the CCD image capturing element 106.

At the CCD image capturing element 106, the fluorescent image Ze is received and subjected to photoelectric conversion depending on the pixels respectively corresponding to the broad-band filter elements 108a and the narrow-band filter elements 108b, whereby the fluorescent image Ze is converted into electric signals and inputted to the image processing unit 130 as similar to the foregoing. The electric signals inputted to the image processing unit 130 are processed by the signal processing circuit 131, then converted into digital signals by the A/D converter circuit 132, and stored into the image memory 135 as the broad-band fluorescent image data and as the narrow-band fluorescent image data.

When the broad-band fluorescent image data and the narrow-band fluorescent image data are obtained, the image generating circuit 137 computes a ratio of signal intensity between the broad-band fluorescent image data and the narrow-band fluorescent image data for each of mutually corresponding pixels, and allots color information corresponding to the ratio to obtain the color image data. Further, image generating circuit 137 allots luminance information to signal intensity of the sampling image data to obtain the luminance image data. The image generating circuit 137 synthesizes those data to generate the synthesized image data and outputs the synthesized image data to the video signal processing circuit 134. The video signal circuit 134 converts the synthesized image data into video signals and outputs the video signals to the monitor 200. The fluorescent diagnostic image 13, which is a pseudo-color image, is thereby displayed on the monitor 200.

Display colors in the fluorescent diagnostic image 13 vary in accordance with variation of relative ratios between the signal intensity of the broad-band fluorescent image data and the signal intensity of the narrow-band fluorescent image data, whereby the fluorescent diagnostic image 13 is displayed by pseudo-colors, in which luminance varies in accordance with the signal intensity of the sampling image data. By setting the pseudo-colors so as to distinguish display colors for fluorescence emitted from normal tissues and fluorescence emitted from diseased tissues, it is possible to display the fluorescence emitted from the normal tissues with a white color and to display the fluorescence emitted from the diseased tissues with a pink color or with other colors. Accordingly, an observer can readily recognize the diseased tissues. Moreover, since the luminance varies in accordance with the signal intensity of the sampling image data, it is possible to display the fluorescent diagnostic image containing the roughness and distance of the observation area of the living body 9.

As described above, the embodiment is arranged to irradiate the ultraviolet light respectively emitted from the LED light sources 111, 112 and 113 onto the fluorescent fibers 114, 115 and 116 to obtain the R light Lr, the G light Lg and the B light Lb, respectively. Therefore, as compared to a case of using a light source device having a xenon lamp, a halogen lamp, metal halides or the like, the illumination unit 110 in the embodiment can be downsized. Moreover, since LED's are considerably less expensive than the xenon lamp, etc., it is possible to reduce the cost of the light source device as compared to the light source device using the xenon lamp, etc. even if a plurality of LED's are arrayed to constitute the LED light sources 111, 112 and 113.

Furthermore, the fluorescent fibers 114, 115 and 116 generate the R light Lr, the G light Lg and the B light Lb, respectively, but do not generate light in a long-wavelength range such as infrared light. Accordingly, it is possible to prevent heat generation at the observation area of the living body 9 attributable to irradiation of the R light Lr, the G light Lg and the B light Lb. Therefore, the CCD image capturing element 106 can be prevented from occurrence of dark noise attributable to the heat at the observation area of the living body 9. As a result, an image with a fine S/N ratio can be obtained.

Moreover, the SLD is used as the sampling light source 121 and the LD is used as the excitation light source 122. Accordingly, the light can be made efficiently incident on the respective fibers 125 and 126 by means of connecting the other ends of the fibers 125 and 126 respectively to the emitting end faces of the sampling light source 121 and the excitation light source 122 directly. As a result, it is possible to emit the sampling light Ls and the excitation light Le with more luminous energy.

Moreover, by forming the fluorescent fibers 114, 115 and 116 respectively as single fibers, it is possible to reduce a diameter of the endoscope inserting portion 100.

When the single fiber is used, the fiber tends to crack easily if a core diameter thereof is relatively large. Therefore, by setting the core diameter thereof within 400 μm, it is possible to prevent the single fiber from cracking easily.

Moreover, each of the R light Lr, the G light Lg and the B light Lb generated from the fluorescent fibers 114, 115 and 116, the sampling light Ls emitted from the sampling light source 121 and the excitation light Le emitted from the excitation light source 122 has small luminous energy as compared to the case of using the light source device having the xenon lamp, etc. Accordingly, there is a risk that an S/N ratio of an obtained image is deteriorated. Therefore, by use of the CCD image capturing element 106 of a charge-multiplying type as the solid-state image capturing element for capturing the optical image of the observation area of the living body 9, it is possible to enhance the image capturing sensitivity by multiplying the signal electrical charges obtained by image capturing even if the luminous energy of the illumination light is weak. As a result, it is possible to enhance the S/N ratio of the obtained image.

In addition, since the mirror tube 103A with a mirror inner surface is used as the illumination optical system 103, it is possible to reduce loss of light which is guided with the light guide 101. In this way, it is possible to magnify the luminous energy of the light to be irradiated onto the observation area of the living body 9.

Figure 4:
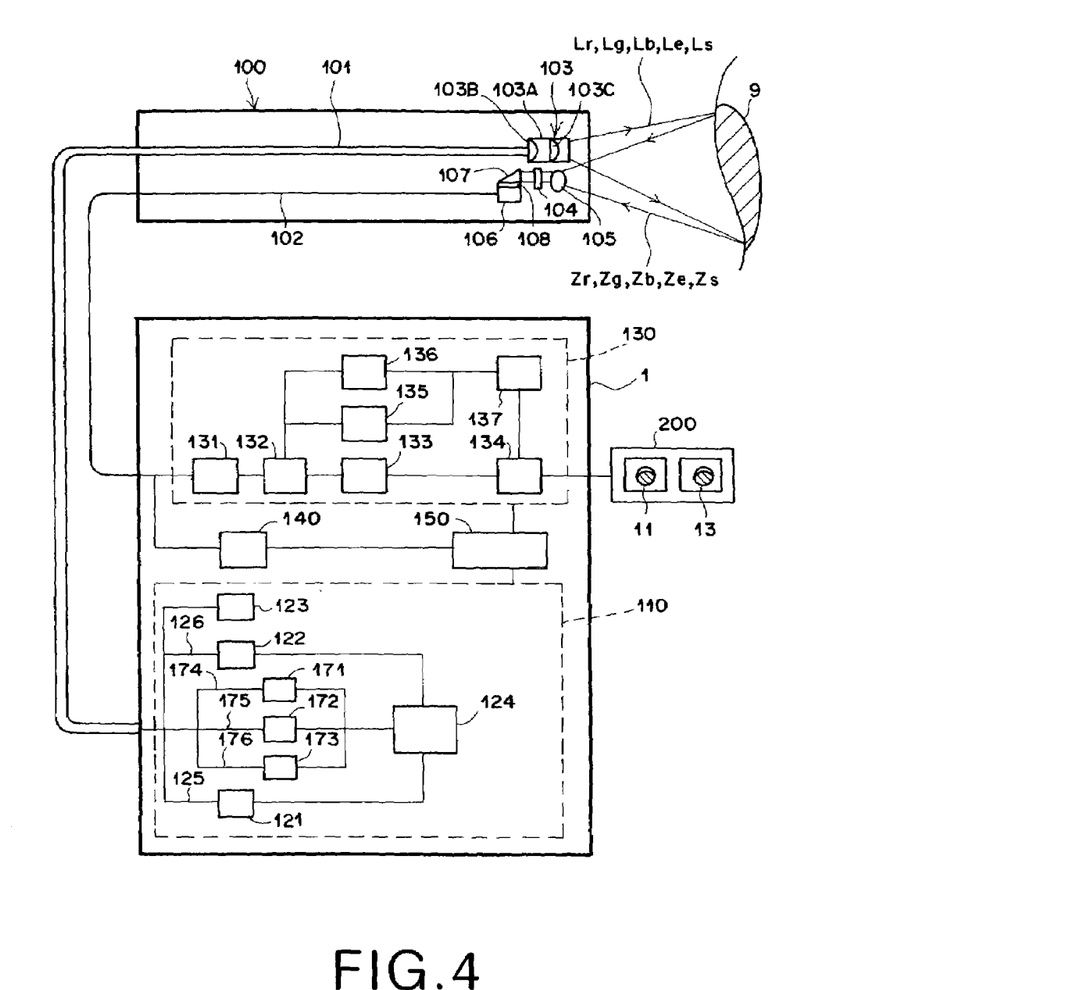
FIG. 4 is a schematic constitutional view showing a constitution of an endoscope using a light source device according to a second embodiment of the present invention.

Next, description will be made regarding a second embodiment of the present invention. FIG. 4 is a schematic constitutional view showing a constitution of an endoscope using a light source device according to the second embodiment of the present invention. In the second embodiment, it is to be noted that members similar to those in the first embodiment are denoted with similar reference numerals and detailed description thereof are omitted.

In the endoscope of the second embodiment, an illumination unit 110 includes light sources 171, 172 and 173 made of either SLD's or LD's for emitting ultraviolet light, and fluorescent fibers 174, 175 and 176 made of single fibers respectively connected to emitting end faces of the light sources 171, 172 and 173 for generating R light Lr, G light Lg and B light Lb by irradiation of the ultraviolet light.

Here, since emitting portions of the SLD's and the LD's have small diameters, the fluorescent fibers 174, 175 and 176 can be connected to the emitting end faces directly. In this way, it is possible to prevent reduction of incident efficiency of the ultraviolet light onto the fluorescent fibers 174, 175 and 176. As a result, it is possible to emit the R light Lr, the G light Lg and the B light Lb with more luminous energy.

Moreover, in the case of connecting the fluorescent fibers 174, 175 and 176 to the emitting end faces of the SLD's or the LD's, incident efficiency is degraded owing to cladding portions between strand cores if the fluorescent fibers 174, 175 and 176 are bundled fibers. Therefore, loss of light attributable to the cladding portions between the strand cores is eliminated by using single fibers for the fluorescent fibers 174, 175 and 176. In this way, it is possible to enhance incident efficiency of the ultraviolet light. As a result, it is possible to emit the R light Lr, the G light Lg and the B light Lb with more luminous energy.

In addition, whereas the LED light sources each composed of a plurality of LED's are used for generating the light of the respective colors in the first embodiment, a single SLD or LD is used for each light source in the second embodiment. Therefore, it is possible to reduce manufacturing costs of the illumination unit 110 as compared to the first embodiment.

Although the above-described embodiments are examples of applying the present invention to endoscopes, the present invention is also applicable to other image capturing devices besides endoscopes.

What is claimed is:

1. An image capturing device comprising:
   a light source device: including at least one light-emitting source having a solid-state light-emitting element for emitting excitation light and at least two fluorescent fibers serially connected for generating illumination light toward an observation area in a given wavelength range owing to irradiation of the excitation light emitted from the solid-state light-emitting element and for emitting the illumination light from one end thereof; and
   a solid-state image capturing means of a charge multiplying type for capturing an optical image based on reflected light emitted from the observation area owing to irradiation of the illumination light.

2. The image capturing device according to claim 1, wherein the solid-state light-emitting element is either of a super luminescence diode and a laser diode, and wherein another end of the fluorescent fiber is connected to an emitting end face of either of the super luminescence diode and the laser diode.

3. The image capturing device according to claim 2, wherein part or all of the light source device and the solid-state image capturing means constitute of an endoscope to be inserted into a living body.

4. An image capturing device as defined in claim 2, wherein the solid-state light-emitting element emits excitation light, having a wavelength less than or equal to 400 nm.

5. The image capturing device according to claim 1, wherein said fluorescent fibers include fibers of respective colors of R, G and B owing to irradiation of the excitation light and receive light from three light-emitting sources for irradiating the excitation light onto said fluorescent fibers respectively.

6. The image capturing device according to claim 5, wherein part or all of the light source device and the solid-state image capturing means constitute an endoscope to be inserted into a living body.

7. An image capturing device as defined in claim 5, wherein the solid-state light-emitting element emits excitation light, having a wavelength less than or equal to 400 nm.

8. The image capturing device according to claim 1, wherein a core diameter of each of the fibers is no more than 400 μm.

9. The image capturing device according to claim 8, wherein part or all of the light source device and the solid-state image capturing means constitute an endoscope to be inserted into a living body.

10. The image capturing device according to claim 1, wherein part or all of the light source device and the solid-state image capturing means constitute an endoscope to be inserted into a living body.

11. The image capturing device of claim 1, wherein a cross-section of each of the fluorescent fibers is taken from a direction perpendicular to a longitudinal direction of said fluorescent fibers includes fibers of respective colors R, G, B.

12. The image capturing device according to claim 11, wherein each of said fibers of respective colors R, G, B is a single fiber.

13. The image capturing device according to claim 12, wherein a core diameter of each single fiber is no more than 400 μm.

14. The image capturing device according to claim 13, wherein part or all of the light source device and the solid-state image capturing means constitute an endoscope to be inserted into a living body.

15. The image capturing device according to claim 12, wherein part or all of the light source device and the solid-state image capturing means constitute an endoscope to be inserted into a living body.

16. An image capturing device as defined in claim 1, wherein the solid-state light-emitting elements emits excitation light, having a wavelength less than or equal to 400 nm.

* * * * *